United States Patent
Fukui et al.

(10) Patent No.: US 9,057,076 B2
(45) Date of Patent: Jun. 16, 2015

(54) COMPOUNDS PURIFIED FROM BLUE ROSES

(75) Inventors: Yuko Fukui, Mishima-gun (JP); Yoshikazu Tanaka, Mishima-gun (JP)

(73) Assignee: SUNTORY HOLDINGS LIMITED, Osaka-shi, Osaka (JP)

( * ) Notice: Subject to any disclaimer, the term of this patent is extended or adjusted under 35 U.S.C. 154(b) by 741 days.

(21) Appl. No.: 13/259,749

(22) PCT Filed: Mar. 25, 2010

(86) PCT No.: PCT/JP2010/055262
§ 371 (c)(1),
(2), (4) Date: Sep. 23, 2011

(87) PCT Pub. No.: WO2010/110382
PCT Pub. Date: Sep. 30, 2010

(65) Prior Publication Data
US 2012/0011771 A1    Jan. 19, 2012

(30) Foreign Application Priority Data

Mar. 27, 2009 (JP) ................................. 2009-080524
May 12, 2009 (JP) ................................. 2009-115722
Jul. 24, 2009 (JP) ................................. 2009-173096

(51) Int. Cl.
| | |
|---|---|
| *C07D 311/62* | (2006.01) |
| *C12N 15/82* | (2006.01) |
| *A01H 5/02* | (2006.01) |
| *C07D 493/16* | (2006.01) |
| *C07H 13/08* | (2006.01) |
| *C12N 9/02* | (2006.01) |
| *C12N 9/10* | (2006.01) |

(52) U.S. Cl.
CPC ............ *C12N 15/825* (2013.01); *A01H 5/0222* (2013.01); *C07D 493/16* (2013.01); *C07H 13/08* (2013.01); *C12N 9/0071* (2013.01); *C12N 9/0073* (2013.01); *C12N 9/1029* (2013.01)

(58) Field of Classification Search
USPC ........................................................ 800/282
See application file for complete search history.

(56) References Cited

U.S. PATENT DOCUMENTS

| | | | |
|---|---|---|---|
| 8,410,335 B2 * | 4/2013 | Tanaka et al. ............... | 800/282 |
| 2010/0281575 A1 | 11/2010 | Tanaka et al. | |
| 2010/0287667 A1 | 11/2010 | Tanaka et al. | |
| 2010/0287668 A1 | 11/2010 | Tanaka et al. | |
| 2011/0088125 A1 | 4/2011 | Togami et al. | |
| 2011/0126320 A1 | 5/2011 | Tanaka et al. | |

FOREIGN PATENT DOCUMENTS

| | | |
|---|---|---|
| EP | 1652916 A1 | 5/2006 |
| JP | 5-184370 | 7/1993 |
| JP | 2002-201372 | 7/2002 |
| JP | 2006512057 A | 4/2006 |
| JP | 2008-253250 | 10/2008 |
| WO | WO-93/01290 A1 | 1/1993 |
| WO | WO-9636716 A1 | 11/1996 |
| WO | WO 2004/020637 * | 3/2004 |
| WO | WO-2004020637 A1 | 3/2004 |
| WO | WO 2005/017147 * | 2/2005 |
| WO | WO-2005017147 A1 | 2/2005 |
| WO | WO-2008120820 A1 | 10/2008 |
| WO | WO-2008156206 A1 | 12/2008 |
| WO | WO-2008156211 A1 | 12/2008 |
| WO | WO-2008156214 A1 | 12/2008 |

OTHER PUBLICATIONS

Supplementary European Search Report mailed Aug. 28, 2012 issued in EP Application No. 10756178.9.
Fukui et al., "Structure of rosacyanin B, a novel pigment from the petals of *Rosa hybrida*", Tetrahedron Letters. vol. 43, No. 14, Apr. 2002, pp. 2637-2639.
Holton et al., "Blue roses—a pigment of our imagination", Trends in Biotechnology, vol. 12, No. 2, Feb. 1, 1994, pp. 40-42.
International Search Report mailed on Apr. 20, 2010 in International Application No. PCT/JP2010/055262 filed Mar. 25, 2010.
(Continued)

*Primary Examiner* — Ashwin Mehta
*Assistant Examiner* — Rebecca Stephens
(74) *Attorney, Agent, or Firm* — Drinker Biddle & Reath LLP

(57) ABSTRACT

Disclosed is a novel compound contained in blue rose. This novel compound, which is contained in blue rose, has a chemical structure represented by general formula (I):

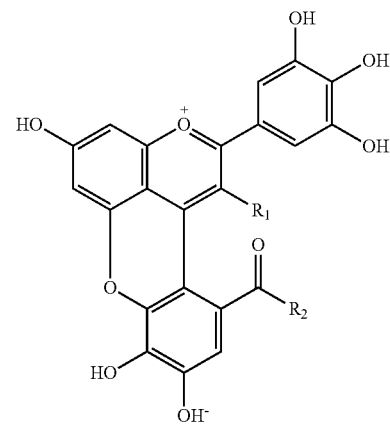

[wherein $R_1$ is a group as set forth in claim 1; and $R_2$ represents —OH, or $R_1$ and $R_2$ together form —O—]. Also disclosed are a rose plant containing the aforesaid compound, and a part of the same.

4 Claims, 12 Drawing Sheets

(56) References Cited

OTHER PUBLICATIONS

Yuko Fukui et al., "Two novel blue pigments with ellagitannin moiety, rosacyanins A1 and A2, isolated from the petals of *Rosa hybrida*", Tetrahedron, vol. 62, No. 41, pp. 9661-9670, (2006).

Timothy A. Holten et al., "Genetics and Biochemistry of Anthocyanin Biosynthesis", The Plant Cell, vol. 7, No. 7, pp. 1071-1083, (1995).

Japanese Office Action mailed Jun. 5, 2012 in Application No. 2011-506120.

* cited by examiner

Fig.13 ¹H NMR OF RED PIGMENT (2)

COMPOUNDS PURIFIED FROM BLUE ROSES

CROSS REFERENCE TO RELATED APPLICATIONS

This application is the National Stage of International Application No. PCT/JP2010/055262 filed Mar. 25, 2010, and claims benefit of Japanese Patent Application Nos. 2009-080524 filed Mar. 27, 2009, 2009-115722 filed May 12, 2009, and 2009-173096 filed Jul. 24, 2009, which are herein incorporated by reference in their entirety.

TECHNICAL FIELD

The present invention relates to a novel compound that is a pigment of a plant, and particularly a rose that has been imparted with the ability to produce delphinidin by genetic recombination, and a plant such as a rose that contains that pigment and a part thereof. In addition, the present invention relates to a method for altering flower color of a plant using that compound.

BACKGROUND ART

Roses are important plants as cut flowers, and their color has been investigated in detail. For example, known examples of anthocyanin-based pigments include cyanidin 3,5-diglucoside, pelargonidin 3,5-diglucoside, cyanidin 3-glucoside, pelargonidin 3-glucoside, peonidin 3,5-diglucoside and peonidin 3-glucoside. The biosynthesis pathways of anthocyanins containing these pigments are known.

In addition, roses that express flavonoid 3',5'-hydroxylase gene due to genetic recombination (refer to Patent Document 1 and Patent Document 2) produce delphin (also referred to as delphidin 3,5-diglucoside). In this case, the hydroxylation reaction at the 5' position of the B ring of the flavonoid is thought to take place at the stage of flavanone or dihydroflavonol. Since flavonoid 3'5'-hydroxylase is a kind of cytochrome P450 present in endoplasmic reticulum, this hydroxylation is assumed to occur on endoplasmic reticulum. In addition to not having a sequence such as a signal peptide, since enzymes such as anthocyanidin glycosyltransferase, which catalyze the biosynthesis reactions of anthocyanins, are soluble proteins, they are present in the cell cytoplasm. Anthocyanins are transported into vacuoles by a pump following glycosylation.

On the other hand, compound rosacyanins (see FIG. 1) have been reported to be present in at least some roses, and the structures of rosacyanins such as rosacyanin A1, rosacyanin B and rosacyanin A2 have been determined (see, for example, Patent Document 3 or Non-Patent Document 1).

Since rosacyanins have a cyanidin backbone in a portion of their structure, there the possibility that they are synthesized based on cyanidin, a common precursor with cyanidin or an analog of cyanidin. However, since this remains to be only speculation, what types of substances are actually used as precursors and what types of pathways are used in synthesis have yet to be clearly determined.

On the other hand, delphinidin is synthesized instead of a portion of the cyanidin in roses in which flavonoid 3',5'-hydroxylase gene is expressed as a result of genetic recombination as previously described. If the aforementioned hypothesis regarding the rosacyanin synthesis pathway, namely that rosacyanin is synthesized by using cyanidin as a precursor, is correct, then rosacyanin would not be synthesized in these genetically modified roses in which cyanidin serving as precursor is essentially absent.

When the inventors of the present invention conducted an analysis to obtain findings regarding rosacyanin synthesis using the aforementioned genetically modified roses that hardly contain any cyanidin or have a considerably decreased cyanidin content in comparison with a host as described in Patent Document 1 or Patent Document 2, contrary to expectations, a novel compound was found to be present having a chemical structure that clearly differed from that of rosacyanins inherently possessed by roses. Moreover, this novel compound was clearly determined to be uniquely present in roses in which flavonoid 3',5'-hydroxylase gene was expressed by genetic recombination, thereby leading to completion of the present invention.

PRIOR ART DOCUMENTS

Patent Documents

Patent Document 1: International Publication WO 2004/020637
Patent Document 2: International Publication WO 2005/017147
Patent Document 3: Japanese Unexamined Patent Publication (Kokai) No. 2002-201372

Non-Patent Documents

Non-Patent Document 1: Tetrahedron, 62, 2006, 9661-9670

SUMMARY OF THE INVENTION

Problems to be Solved by the Invention

An object of the present invention is to provide a novel compound that is a pigment of a plant, and particularly a rose that has been imparted with the ability to produce delphinidin by genetic recombination, and a plant such as a rose that contains that pigment, and a part thereof. In addition, an object of the present invention is to provide a method for altering the flower color of a plant using that compound.

Means for Solving the Problems

The present invention is as described below.
[1] A compound represented by the following general formula (I):

[Chemical Formula 1]

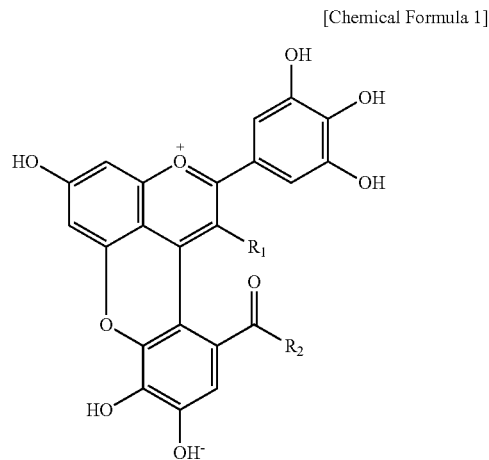

wherein, $R_1$ represents the following group:

[Chemical Formula 2]

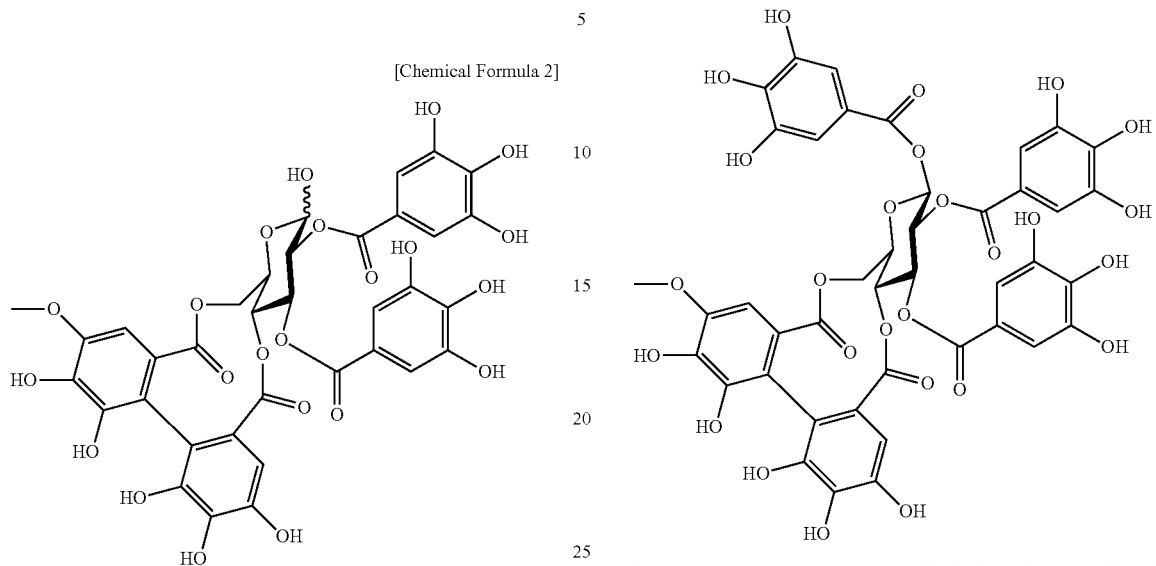

and $R_2$ represents —OH or $R_1$ and $R_2$ together form —O—, or $R_1$ represents the following group:

[Chemical Formula 3]

and $R_2$ represents —OH, provided that the coordination (wavy line) of the hydroxyl group at position 1 of glucose in $R_1$ exhibits tautomerism between the α form and the β form.

[2] A compound represented by the following formula:

[Chemical Formula 4]

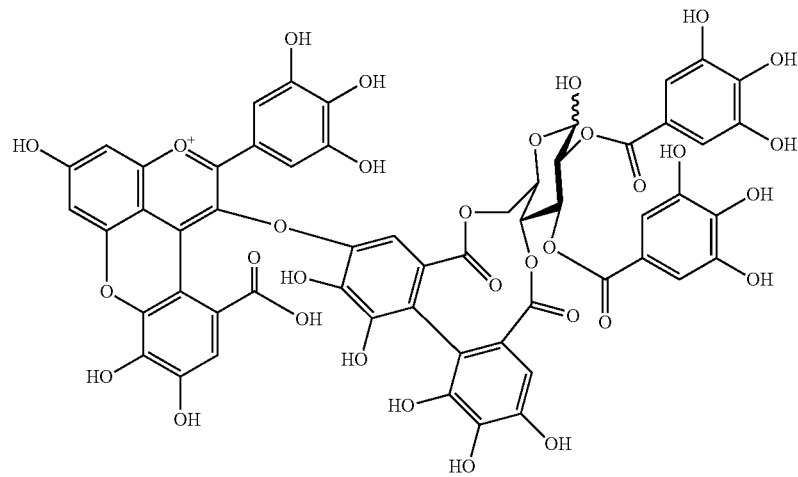

[3] A compound represented by the following formula:

[Chemical Formula 5]

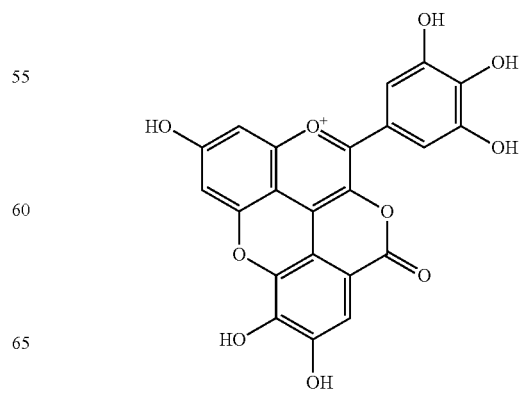

[4] A compound represented by the following formula:

[Chemical Formula 6]

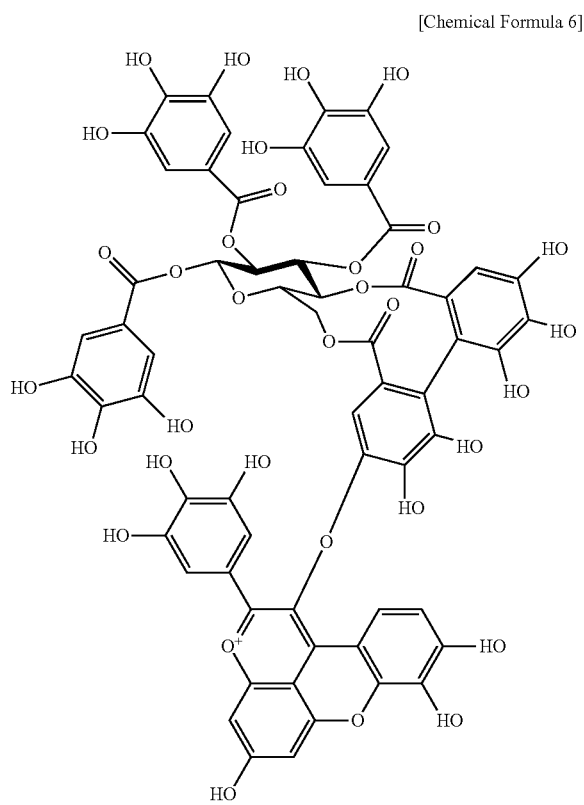

[5] A plant containing the compound described in any of [1] to [4] above, provided that the plant does not contain the compound naturally.
[6] The plant described in [5] above that is a member of the family Rosaceae.
[7] The plant described in [6] above, wherein the plant that is a member of the family Rosaceae is plant of the family Rosaceae, genus *Rosa*.
[8] The plant described in [7] above, wherein the plant of the family Rosaceae, genus *Rosa* is a rose.
[9] A part of the plant described in any of [5] to [8] above.
[10] The part of the plant described in [9] above that is a cut flower.
[11] A cut flower processed product that uses the cut flower described in [10] above.
[12] A method for altering flower color of a plant using the compound described in any of [1] to [4] above.
[13] The method described in [12] above, wherein the plant is a member of the family Rosaceae.
[14] The method described in [13] above, wherein the plant that is a member of the family Rosaceae is plant of the family Rosaceae, genus *Rosa*.
[15] The method described in [14] above, wherein the plant of the family Rosaceae, genus *Rosa* is a rose.

Effects of the Invention

According to the present invention, a novel pigment present in the petals of blue rose was extracted, isolated and purified, and the chemical structure thereof was elucidated. This is based on research involving genetically altering rose color and creating a novel plant of the Rosaceae family. In addition, the novel pigment according to the present invention can be used, for example, to improve the color of cut flowers by being absorbed into a rose or other cut flower, and can also be used to color foods and beverages, for example, as a natural plant pigment.

EMBODIMENTS OF THE INVENTION

The novel pigment according to the present invention has a structure in which one hydroxyl group is further added to the B ring of a known substance in the form of rosacyanin A1, rosacyanin B and rosacyanin A2 (in which the number of hydroxyl groups of the B ring is 2). In other words, the novel blue pigment according to the present invention can be said to be a novel compound having a partial structure of blue pigment deiphinidin, which is a known substance that has been confirmed to be present in blue roses (in which the number of hydroxyl groups of the B ring is 3).

As is described in Patent Document 1 or 2, blue pigment not present in conventional rose varieties (having three hydroxyl groups on the B ring) is present in blue roses due to the function of a blue gene (flavonoid 3',5'-hydroxylase). At present, compounds having a structure in which one hydroxyl group is further added to the B ring of known substances in the form of rosacyanin A1, rosacyanin B and rosacyanin A2 (in which the number of hydroxyl groups of the B ring is 2) have been isolated and purified as such blue pigments, they have been identified by TOF-MS and NMR, and their structures have been determined.

Figure 3:
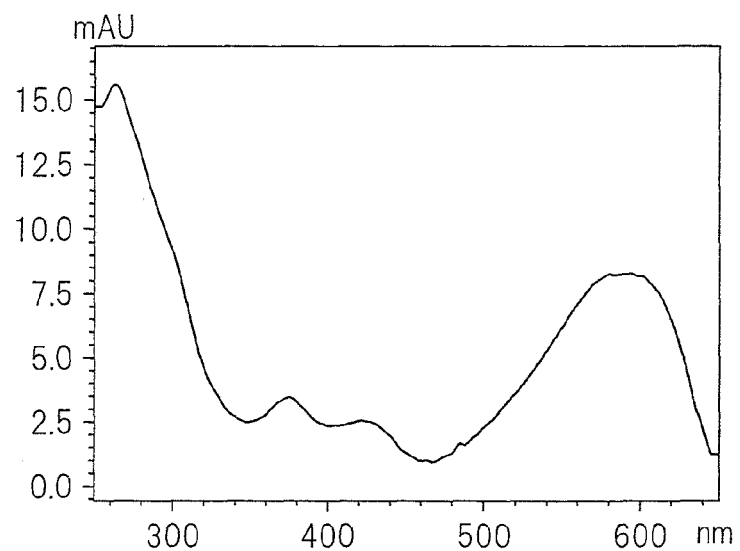
FIG. 3 is a graph of the visible to ultraviolet absorption spectrum of a blue pigment (1) in 30% acetonitrile and 0.5% TFA.
Figure 4:
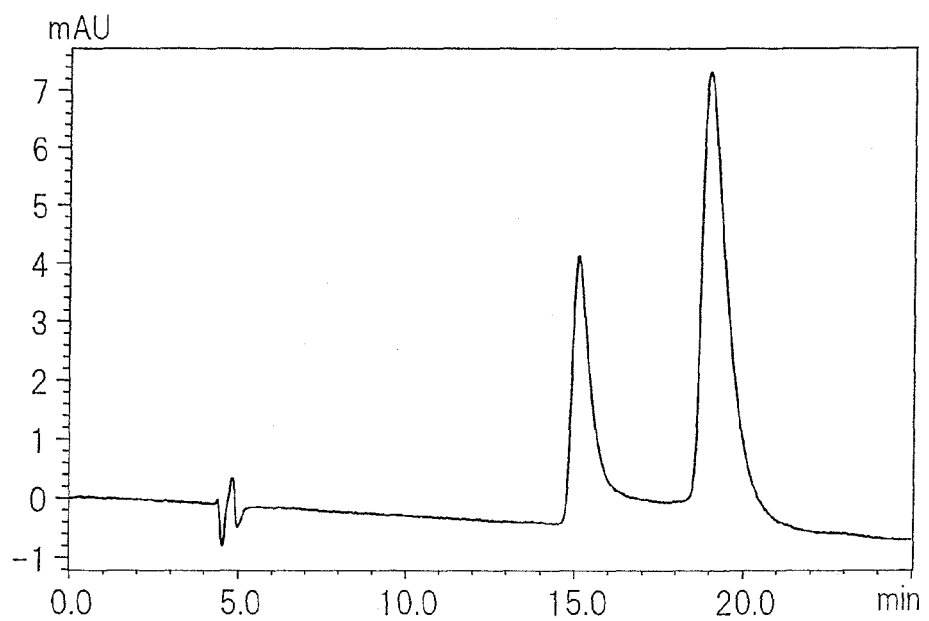
FIG. 4 is a chromatogram obtained during analysis of a blue pigment (1) by HPLC, wherein two peaks are observed as a result of the hydroxyl group at position 1 of glucose exhibiting tautomerism between the α form and the β form.
Figure 5:
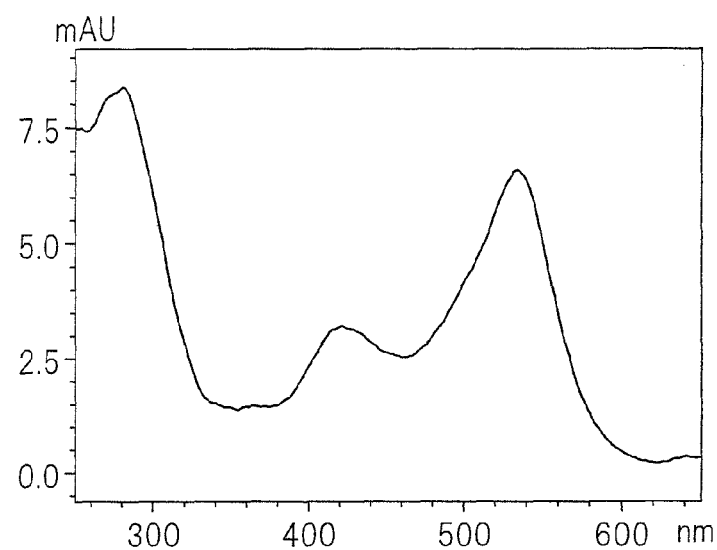
FIG. 5 is a graph of the visible to ultraviolet absorption spectrum of a red pigment (2) in 30% acetonitrile and 0.5% TFA.
Figure 6:
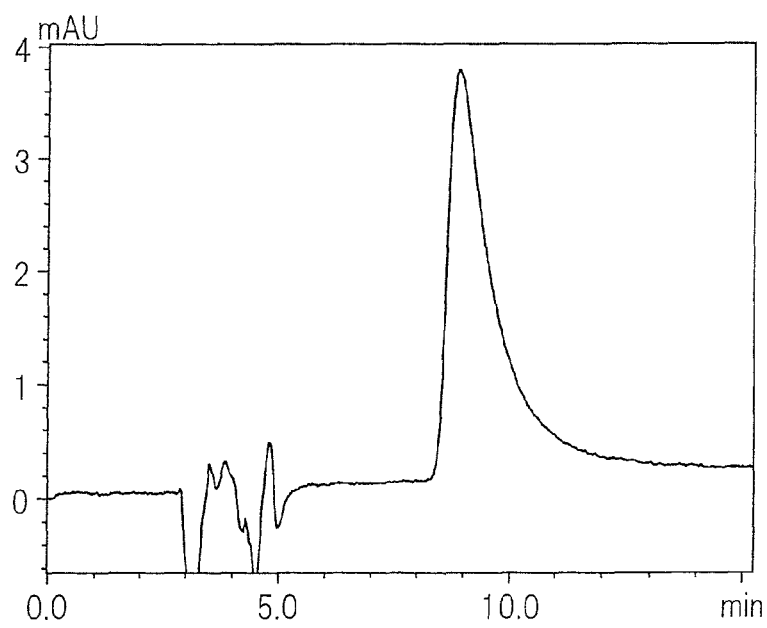
FIG. 6 is a chromatogram obtained during analysis of a red pigment (2) by HPLC.
Figure 7:
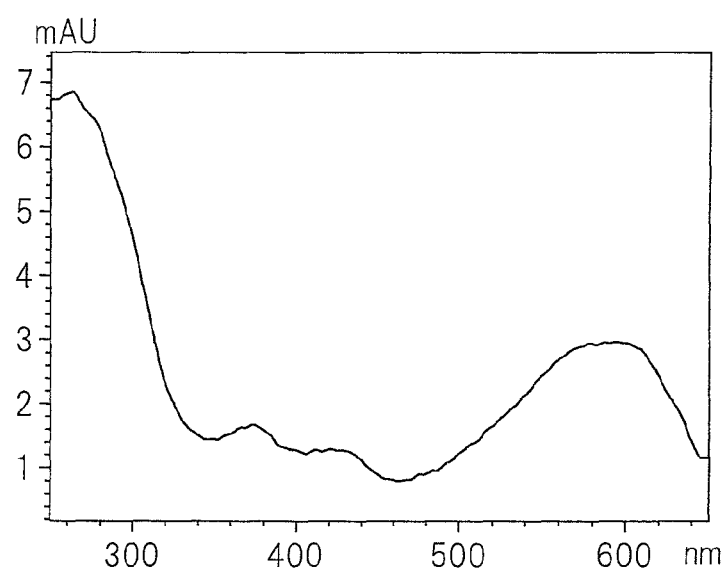
FIG. 7 is a graph of the visible to ultraviolet absorption spectrum of a blue pigment (3) in 30% acetonitrile and 0.5% TFA.
Figure 9:
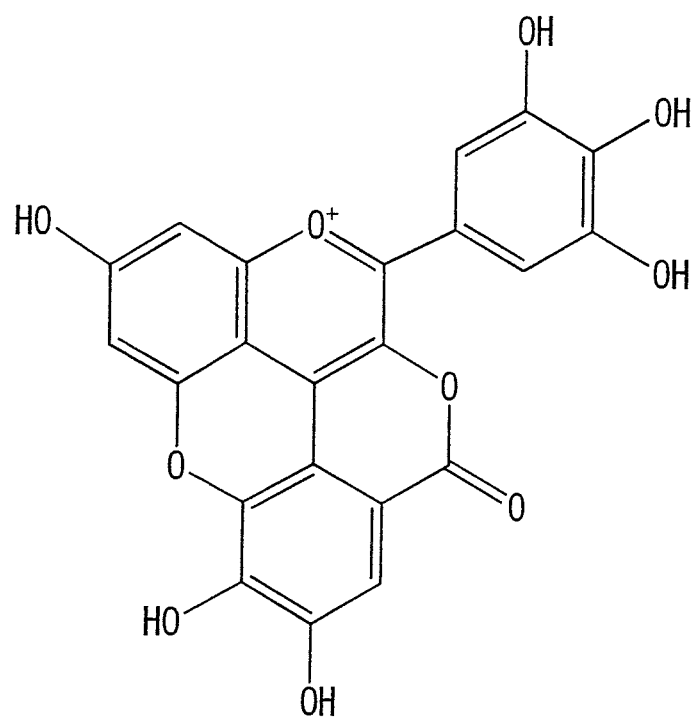
FIG. 9 indicates the chemical structural formula of a red pigment (2).
Figure 11:
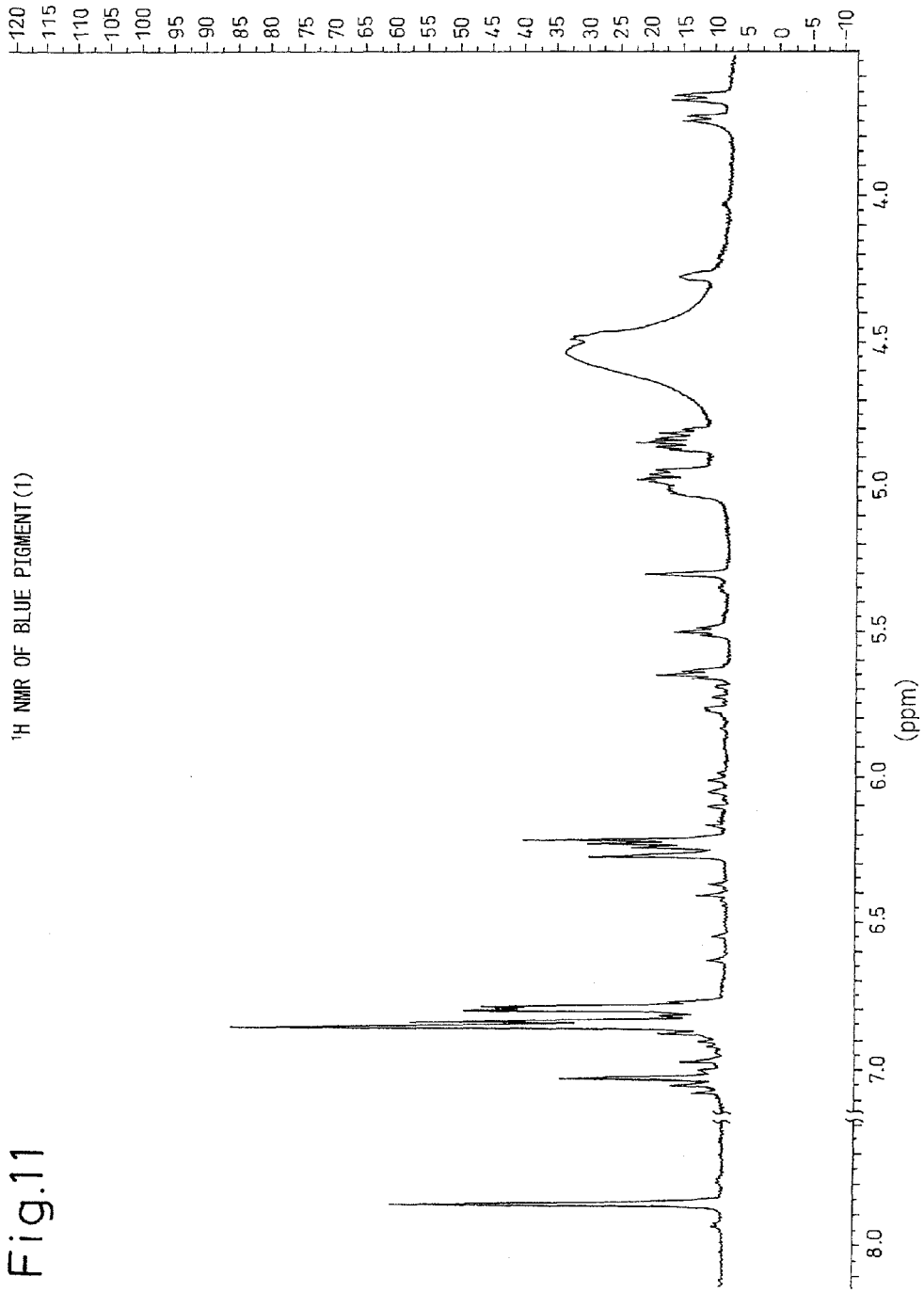
FIG. 11 is a chart of the $^1$H-NMR spectrum of the blue pigment (1) shown in FIG. 8.

The three types of compounds of the present invention are either compounds yielding the data indicated in FIGS. 3, 4, 11 and/or 12, respectively, compound yielding the data shown in FIGS. 5, 6, 9 and/or 13, respectively, or compounds yielding the data shown in FIG. 7.

As a result of further enhancing the effect of improving solubility due to having three hydroxyl groups as a result of further adding a hydroxyl group to the B ring thereof, anthocyanins such as rosacyanins having a larger molecular weight than cyanidin are thought to be more effective pigments in terms of being transported to vacuoles of flower petal cells and demonstrating blue color. In addition, rosacyanins are characterized as being superior to ordinary pigments in terms of being synthesized in the plant body. In addition, the present invention provides a plant containing a compound indicated in FIGS. 8 to 10. However, the plant does not naturally contain the compound or the compound is not present in the flower petals thereof in a detectable amount. In addition, the present invention provides a method for altering plant flower color using the compound shown in FIGS. 8 to 10. For example, the compound according to the present invention can only be acquired by transfecting a gene of an enzyme involved in synthesis of the compound according to the present invention into a target plant using genetic engineering techniques, and then synthesizing a detectable prescribed amount of the compound in flower petals of the plant. Alternatively, although the compound according to the present invention can also be acquired by a physical method such as by absorbing the compound according to the present invention directly into a plant, the manner in which the target plant contains the compound is not limited thereto.

Figure 8:
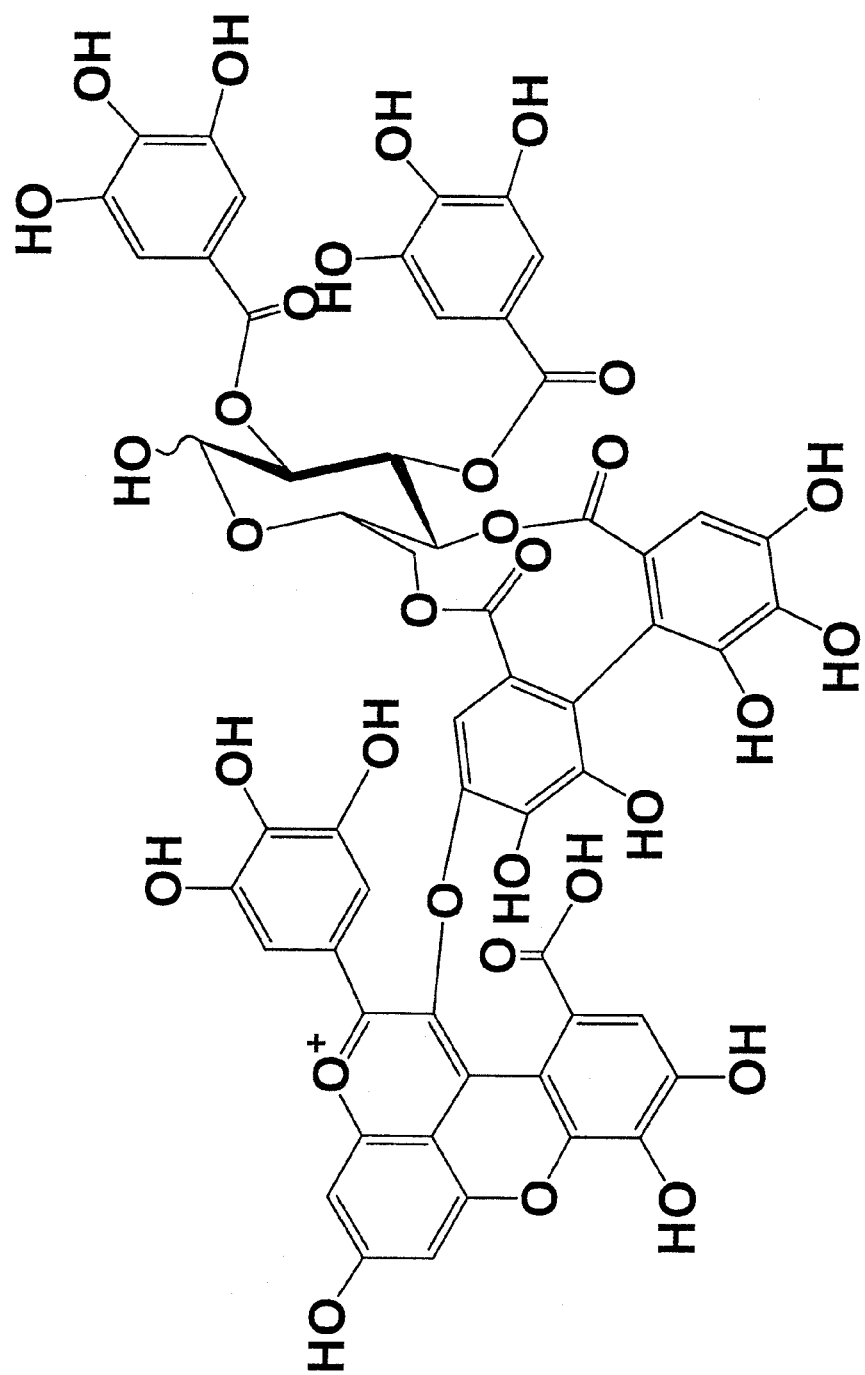
FIG. 8 indicates the chemical structural formula a blue pigment (1), wherein coordination (wavy line) of the hydroxyl group of glucose exhibits tautomerism between the α form and the β form.
Figure 10:
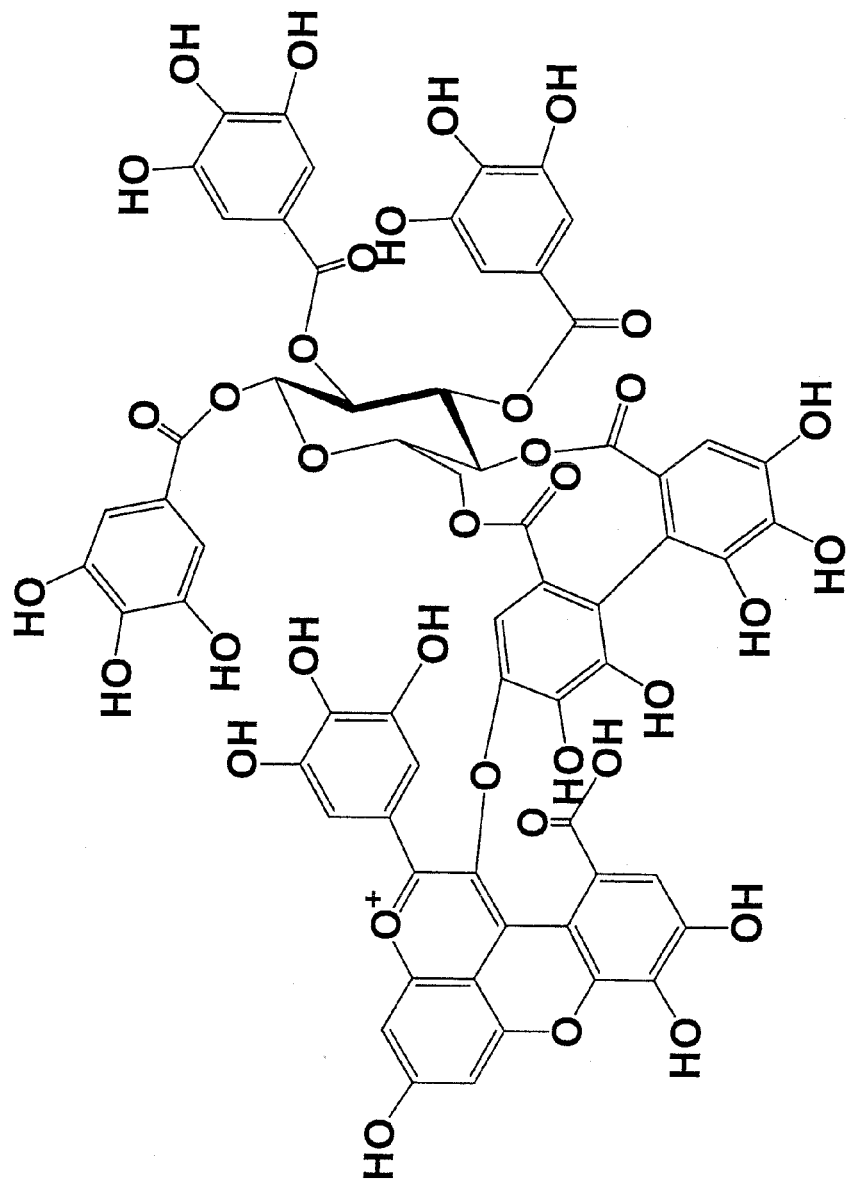
FIG. 10 indicates the chemical structural formula of a blue pigment (3).

The plant body of the present invention contains a compound indicated in FIGS. 8 to 10 in the flower petals thereof. Although there are no particular limitations on the content of the compound in the flower petals of the plant body, it is preferably 0.00001 mg/g or more based on the wet weight of the flower petals. The lower limit of the content of the compound is more preferably 0.0001 mg/g or more and even more preferably 0.0007 mg/g or more. The upper limit of the content of the compound is preferably 1 mg/g or less, more preferably 0.5 mg/g or less and even more preferably 0.13 mg/g or less.

Examples of target plants include, but are not limited to, roses, chrysanthemums, carnations, snapdragons, cyclamens, orchids, prairie gentians, freesia, gerbera, gladiolas, baby's-breath, kalanchoe, lilies, pelargonium, geraniums, petunias, torenia, tulips, rice, barley, wheat, rapeseed, potato, tomato, poplar, banana, eucalyptus, sweet potato, soybeans, alfalfa, lupines, corn and cauliflower.

Preferable examples of these target plants include plants of the family Rosaceae, more preferably plants of the family Rosaceae, genus *Rosa*, and even more preferably roses as exemplified by *Rosa hybrida*. The present invention relates to portions of the aforementioned plants, and particularly cut flowers and flower processed products using the cut flowers. Here, cut flower processed products include, but are not limited to, pressed flowers, preserved flowers, dry flowers and resin-sealed products using these cut flowers.

EXAMPLES

The following provides a more detailed explanation of the present invention through examples thereof.

Example 1

Isolation and Purification of Pigment Compound

The pigment compound of the present invention was purified and isolated by using blue rose for the extraction source.

Production of Lavande Variety Transfected with Plasmid pSPB919

A blue rose was produced for use as the extraction source. A Lavande variety was produced that was transfected with plasmid pSPB919 according to the method described below.

RNA was obtained from the petals of blue iris cut flowers and poly-A RNA was further prepared from the RNA. A cDNA library using λ2ZAPII (Stratagene) as a vector was prepared from this poly-A RNA using a cDNA library preparation kit (Stratagene) according to the method recommended by the manufacturer. A DRF gene fragment of iris was acquired in the same manner as a report describing the acquisition of a DFR fragment from Japanese gentian (Tanaka, et al., Plant Cell Physiol., 37, 711-716, 1996).

The resulting roughly 400 bp DNA fragment was recovered with GeneClean according to the method recommended by the manufacturer, and sub-cloned to pCR-TOPO. When nucleotide sequence thereof was determined, the sequence was found to be homologous with rose DFR gene. The iris cDNA library was then screened using this DNA fragment to obtain iris DFR cDNA containing the full length of the amino acid sequence. The entire nucleotide sequence of cDNA contained in a clone designated as pSPB906 was then determined (refer to SEQ ID NO. 9 and SEQ ID NO. 10 of Patent Document 2 for the nucleotide sequence and amino acid sequence).

Next, a roughly 3.9 kb DNA fragment obtained by digesting pSPB580 with BamHI and XhoI and a roughly 1.5 kb DNA fragment obtained by digesting pSPB906 with BamHI and XhoI were ligated and the resulting plasmid was designated as pSPB909.

Transcription of double-stranded RNA of the rose DFR cDNA was carried out in plants in the following manner. A roughly 3.5 kb DNA fragment (containing a Mac1 promoter, rose DFR cDNA and mas terminator) obtained by partially digesting pCGP1364 (Tanaka, et al., Plant Cell Physiol., 36, 1023-1031, 1995) with PstI was inserted into the PstI site of pUC19 (Yanisch-Perron, C. et al., Gene, 33, 103-119, 1985), and the portion of the resulting plasmid in which the HindIII site of pUC19 was close to the MacI promoter was designated as pCGP1394.

Next, a roughly 1.4 kb DNA fragment obtained by digesting pCGP1394 with HindIII and SacII, a roughly 1.9 kb DNA fragment obtained by digesting pCGP1394 with PstI followed by blunting and further digesting with SacI, and a binary vector fragment obtained by digesting pBinPLUS with SacI followed by blunting and further digesting with HindIII were ligated to obtain pSPB185. The pSPB185 was then digested with XbaI, blunted and ligated with SalI linker to obtain pSPB521. A roughly 700 bp DNA fragment obtained by digesting pUE6 with HindIII and BamHI, a binary vector DNA fragment obtained by digesting pSPB521 with HindIII and SacI, and a GUS gene DNA fragment obtained by digesting pE2113 with BamHI and SacI were ligated to obtain pSPB528.

pSPB528 is a binary vector capable of inserting a structural gene between cauliflower mosaic virus 35S having an enhancer and a mannopine synthase terminator and expressing in a plant. In addition, since it shortens the sequence of the 5'-untranslated region of rose DFR cDNA contained in pCGP645, pCGP645s was obtained by digesting pCGP645 with SmaI and PvuI followed by blunting and ligation.

The 5'-side sequence of rose DFR cDNA was acquired by amplifying by PCR using pCGP645s as template and using a reverse primer and synthesis primer RDF310 (refer to SEQ ID NO. 19 of Patent Document 2) as primers, and then cloning to pCRTOPO. The DNA nucleotide sequence was determined and confirmed to be of errors attributable to PCR. This was designated as pSPB569. In addition, a different length of a rose DFR cDNA 5'-side sequence was acquired by amplifying by PCR using pCGP645s as template and using a reverse primer and synthesis primer RDF830 (refer to SEQ ID NO. 20 of Patent Document 2) as primers, followed by cloning to pCRTOPO. The DNA nucleotide sequences was determined and confirmed to be free of errors attributable to PCR.

This was designated as pSPB570. A binary vector DNA fragment obtained by digesting pSPB528 with BamHI and SacI, a roughly 0.3 kb DNA fragment obtained by digesting pSPB569 with SacI and XhoI, and a DNA fragment obtained by digesting pSPB570 with BamHI and SalI were ligated to obtain pSPB572. This vector is designed so as to transcribe double-stranded RNA of rose DFR cDNA in plants.

pUE6 was digested with SacI and blunted followed by the insertion of an SalI linker to obtain pUE8. A DNA fragment obtained by digesting pUE8 with HindIII and EcoRI was transfected into the HindIII and EcoRI sites of pBinPLUS to pSPB189. A roughly 3.7 kb DNA fragment obtained by digesting pSPB189 with BamHI and SalI and a roughly 1.8 kb DNA fragment obtained by completely digesting pCGP1961 with BamHI and further partially digesting with XhoI were ligated to obtain pSPB567. After digesting pSPB572 with PacI and subjecting to dephosphorylation treatment, a roughly 2.8 kb DNA fragment obtained by digesting pSPB567 with PacI was ligated, and a plasmid that was transcribed in the same direction as nptII gene and pansy-derived F3'5'H#40 was selected and designated as pSPB905.

Figure 1:
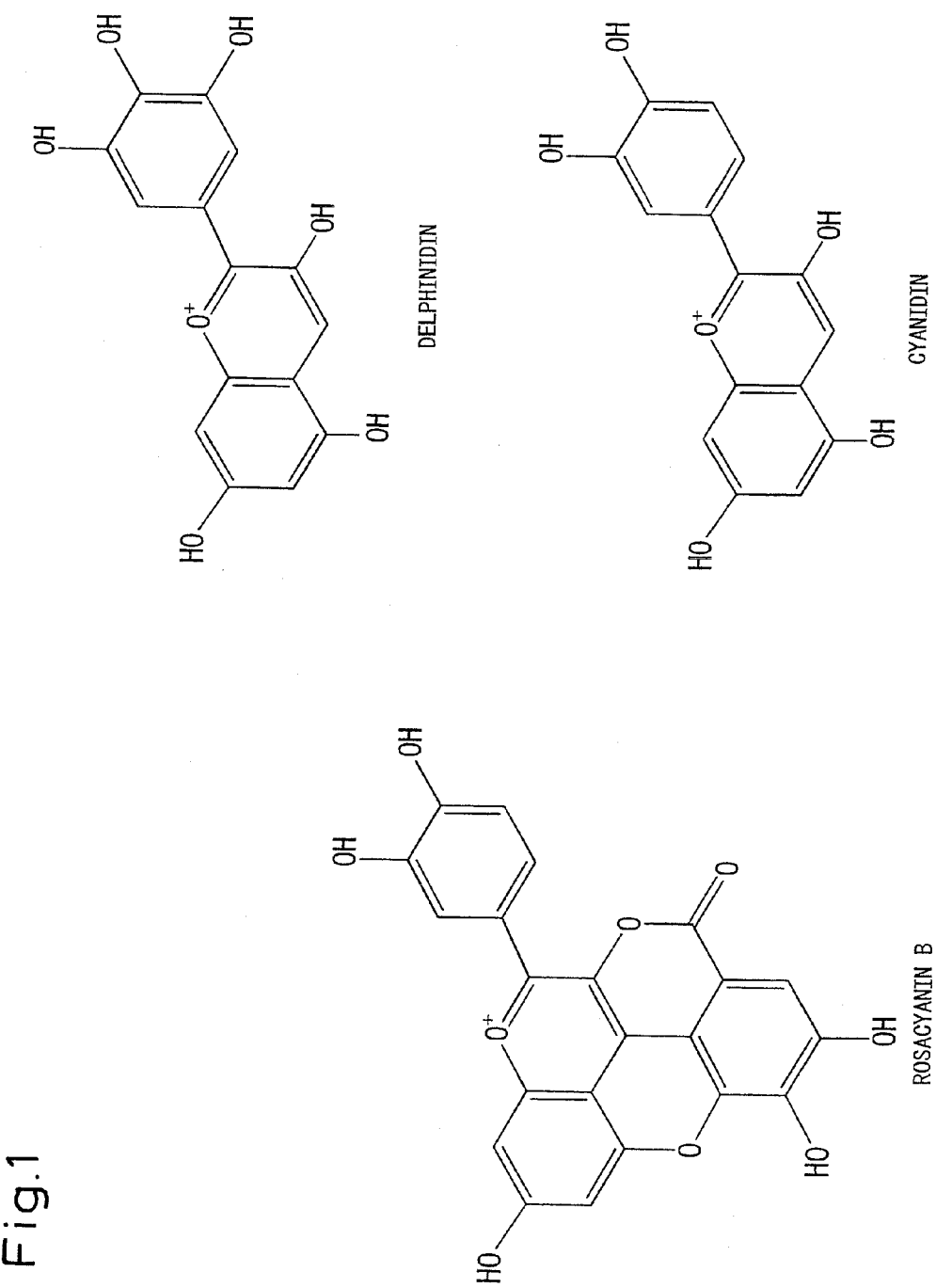
FIG. 1 indicates the chemical structural formulas of cyanidin, delphinidin and rosacyanin.
Figure 2:
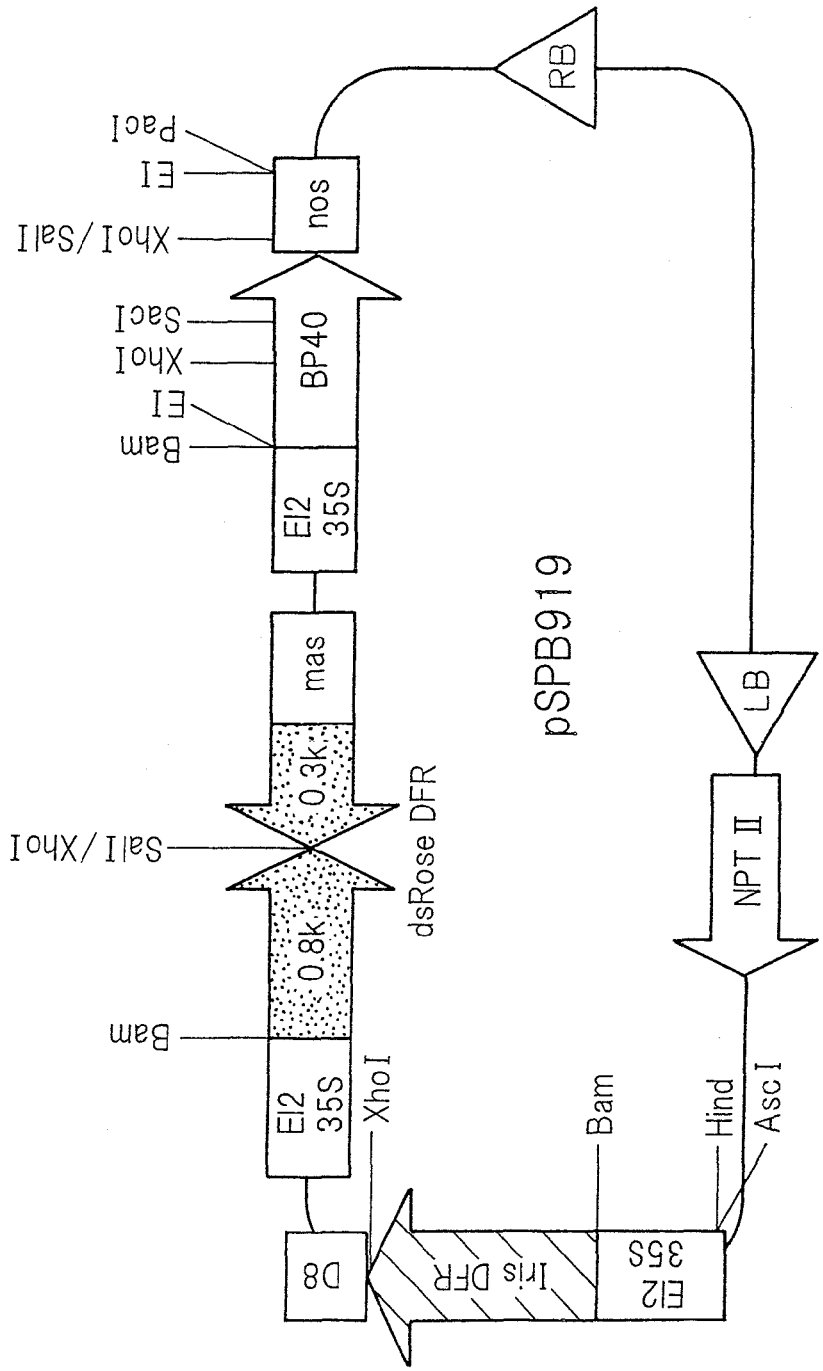
FIG. 2 indicates the structure of plasmid pSPB919 transfected into the mauve rose variety "Lavande".

After digesting pSPB905 with AscI and subjecting to dephosphorylation treatment, a roughly 2.5 kb DNA fragment obtained by digesting pSPB909 with AscI was ligated to obtain a plasmid in which iris DFR gene is transcribed in the same direction as nptII gene, and this plasmid was designated as pSPB919 (see FIG. 2). This plasmid is expected to transcribe iris-derived DFR gene and pansy-derived F3'5'H#40 gene in roses, and control expression of rose DFR gene by transcription of double-stranded RNA. This plasmid was transfected into Agrobacterium tumefaciens strain Ag10.

pSPB919 (see FIG. 2) was transfected into mauve rose variety "Lavande" by infecting the Agrobacterium to obtain a transgenic plant. The transformed cells were then regenerated to obtain a transgenic plant in the form of the blue rose (variety Lavande transfected with plasmid pSPB919) and this was then allowed to bloom.

Extraction, Isolation, Purification and Identification of Pigment Compounds

Pigment compounds were purified from 230 g of flower petals of the blue rose obtained in the manner described above (Lavande variety transfected with plasmid pSPB919) according to the method described below.

230 g of flower petals were frozen and crushed in liquid nitrogen using a homogenizer followed by the addition of 1 liter of 50% acetonitrile containing 0.5% TFA and soaking overnight. A filtrate obtained by filtering with diatomaceous earth was concentrated to about ⅔ the original volume with a rotary evaporator.

This concentrated extract was applied to 400 ml of an adsorption resin HP-20 (Mitsubishi Chemical). After rinsing with 800 ml of water, the extract was sequentially eluted with 1 liter of 20% acetonitrile containing 0.1% TFA and 60% acetonitrile containing 0.1% TFA. A fraction containing blue pigment eluted in the 60% fraction.

This fraction was then purified by preparative HPLC. The Develosil ODS-UG column (Nomura Chemical, 5 cm in diameter×50 cm) was used for the column, the mobile phase consisted of water for A and 50% acetonitrile containing 0.5% TFA for B, the flow rate was 32 ml/min, and the linear concentration gradient consisted of 30% B (held for 30 minutes), increasing from 30% B to 100% B (50 minutes) and then holding at 100% B for 20 minutes. Detection was carried out at 260 nm. The fraction containing blue pigments that eluted from 67 minutes to 82 minutes was collected and freeze-dried. Chromatography was repeated twice.

1.2 g of the freeze-dried product was applied to a Sephadex LH-20 column (Pharmacia) (1.2 liters) equilibrated with 50% acetonitrile. After eluting 2.5 liters of 50% acetonitrile, a fraction containing blue pigment further eluted with 2.5 liters of 50% acetonitrile was collected and freeze-dried.

Preparative HPLC was again carried out on the resulting freeze-dried product.

A YMC Pack Polymer C18 column (YMC, 2 cm in diameter×30 cm) was used for the column, the mobile phase consisted of 0.5% TFA in water for A and 0.5% TFA in 50% acetonitrile for B, the flow rate was 6 ml/min, and chromatography was carried out using the following concentration gradient: 65% B (held for 30 minutes), increasing from 65% B to 90% B (20 minutes) and then holding at 90% B for 30 minutes. Detection was carried out at 260 nm. A red pigment (2) that eluted at 50 to 52 minutes, a blue pigment (1) that eluted at 60 to 65 minutes, and a blue pigment (3) that eluted at 65 to 73 minutes were collected and freeze-dried. Chromatography was repeated a total of three times.

The freeze-dried product, the blue pigment (1), the red pigment (2) and the blue pigment (3) obtained in the manner described above were visually observed for color tone. As a result, they demonstrated a deep blue, deep red, and deep blue color, respectively.

Among these, when the content of the blue pigment (1) in the flower petals was measured, the content thereof was found to be within the range of 0.0007 mg/g to 0.13 mg/g based on the wet weight of the flower petals.

Example 2

Structural Analysis of Pigment Compounds by Instrumental Analysis

The blue pigment (1), the red pigment (2) and the blue pigment (3) were subjected to various instrumental analyses using re-purified samples as necessary.

The blue pigment (1), the red pigment (2) and the blue pigment (3) were analyzed by HPLC, and their absorption spectra at 650 nm to 250 nm in 30% acetonitrile and 0.5% TFA were measured with a photodiode array detector (see FIGS. 3, 5 and 7).

HPLC was carried out by using a Shodex Asahipak ODP50 column (Showa Denko, 4.6 mm in diameter×25 cm) for the column and isocratic elution of a mobile phase consisting of 30% acetonitrile and 0.5% TFA at a flow rate of 0.6 ml/min. Detection was carried out by measuring the absorption spectra at 650 nm to 250 nm with a photodiode array detector (SPDM10Avp, Shimadzu) and monitoring the chromatogram at A560 nm.

The results are summarized below (refer to FIGS. 4 and 6 for retention times (R.T.).

Blue pigment (1) λmax 593 nm R.T. 14.6 and 18.5 min*
Red pigment (2) λmax 535 nm R.T. 8.9 min
Blue pigment (3) λmax 594 nm R.T. 21.6 min

*: Blue pigment (1) exhibited two peaks as a result of the hydroxyl group at position 1 of glucose demonstrating tautomerism between the α form and the β form.

TOF-MS measurements were carried out on the blue pigment (1), the red pigment (2) and the blue pigment (3).

MS was carried out by measuring in the positive V mode using the Q-TOF Premier (Micromass, U.K.) equipped with a Z-spray ion source. MS was carried out using a cone voltage of 60 V and a capillary voltage of 3 KV, mass calibration was carried out by lock spray, and leucine enkephalin (m/z: 556.2771 [M+H]+) was used for the reference.

As a result, the blue pigment (1) showed molecular ions of m/z=1221.1352 $[M]^+$, the red pigment (2) showed molecular ions of m/z=435.0380 $[M]^+$ and the blue pigment (3) showed molecular ions of m/z=1373.1442 $[M]^+$, and closely agreed with the molecular formulas $C_{56}H_{37}O_{32}$ (error: +6.9 ppm), $C_{22}H_{11}O_{10}$ (error: +6.4 ppm) and $C_{63}H_{41}O_{36}$ (error: +4.6 ppm), respectively.

The absorption spectra of the blue pigment (1), the red pigment (2) and the blue pigment (3) in 30% acetonitrile containing 0.5% TFA are shown in FIGS. 3, 5 and 7, respectively.

The absorption maxima in the visible range of the blue pigment (1) and the blue pigment (3) had shifted somewhat to a longer wavelength than the absorption maximum of the compound of formula (II) described in Example 1 of Patent Document 3.

The compound of formula (II) described in Patent Document 3 demonstrates a blue color as described in Patent Document 3. However, since the absorption maxima of the blue pigment (1) and the blue pigment (3) obtained had an even longer wavelength than the absorption maximum of the compound of formula (II) described in Patent Document 3, they demonstrate a deeper blue color than the compound of formula (II). Accordingly, the blue pigment (1) and the blue pigment (3) newly discovered in the present invention were clearly determined to be effective in imparting a deeper blue color to plants. When the molecular weight of the blue pigment (1) was measured by TOF-MS, it was found to yield a value of m/z=1221.13 $[M]^+$, which is 16 mass units greater than the molecular weight of 1205 of the compound of formula (II) described in Example 1 of Patent Document 3. This indicates that the pigment compound having a molecular weight that is 16 mass units larger than the known pigment compound of Patent Document 3 is contained in the Lavande variety transfected with plasmid pSPB919 described in Patent Document 2. Since the increase in molecular weight caused by the hydroxylation reaction by flavonoid 3',5'-hydroxylase is an increase of 16 mass units resulting from the addition of a single oxygen atom, the blue pigment (1) was thought to have one more oxygen atom than the compound represented by formula (II) described in Example 1 of Patent Document 3. Since flavonoid 3'5'-hydroxylase specifically hydrolyzes the B ring of flavonoids, the compound identified here was judged not to be the rosacyanin A1 glycoside described in Non-Patent Document 1, but rather a compound having a partial structure of delphinidin that has 3 hydroxyl groups on the B ring. Namely, the structures of the blue pigment (1), the red pigment (2) and the blue pigment (3) were judged to be the structures shown in FIGS. 8, 9 and 10, respectively.

In addition, each of the compounds was measured by NMR. The compounds were dissolved in DMSO-d6((($CD_3$)$_2$SO)dimethylsulfoxide) containing 1% DCl (deuterium chloride), and residual peaks of $^1H$ and $^{13}C$ at δ2.50 and δ39.43 were used as internal standards. Measurement parameters consisted of $^1$H-NMR, $^1$H{$^{13}$C}-HSQC, $^1$H{$^{13}$C}-HMBC, TOCSY, DQF-COSY and ROE, and the parameters were measured with a DMX-750 Spectrometer (Bruker Biospin, Germany). As a result, the structures indicated in FIGS. 8, 9 and 10 were determined for the blue pigment (1), the red pigment (2) and the blue pigment (3), respectively.

Figure 12:
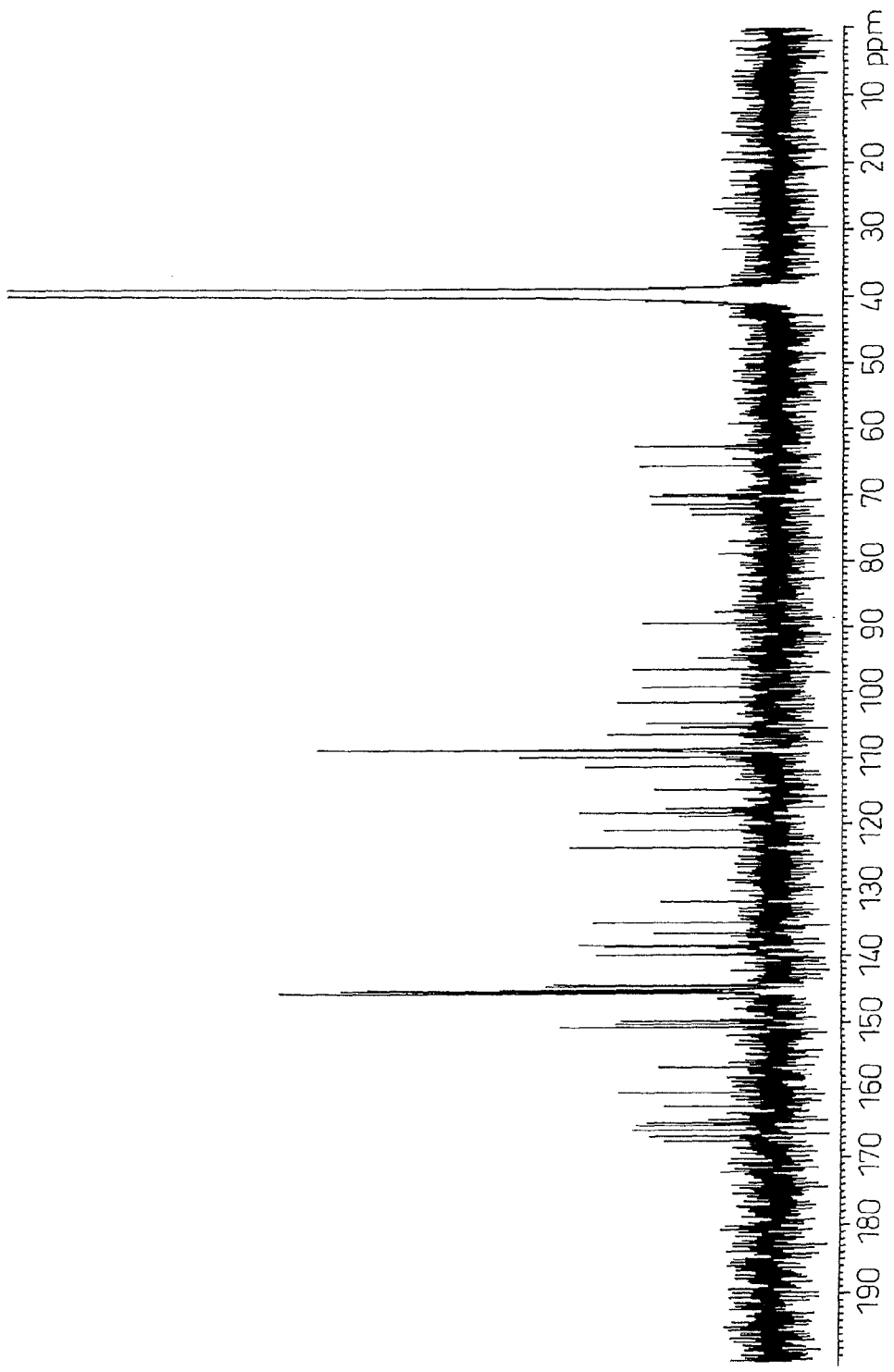
FIG. 12 is a chart of the $^{13}$C-NMR spectrum of the blue pigment (1) shown in FIG. 8.

The results of $^1$H-NMR analysis of the blue pigment (1) are shown in FIG. 11, while the results of $^{13}$C-NMR analysis are shown in FIG. 12.

In the case of the blue pigment (1), signals during $^1$H-NMR were observed at δ3.67 (1H, d12, Glc-6α), δ4.48 (1H, dd2, 9, Glc-5α), δ4.84 (1H, t9, Glc-4α), δ4.94 (1H, dd2, 9, Glc-2α), δ4.99 (1H, dd2, 12, Glc-6α), δ5.30 (1H, d2, Glc-1α), δ5.64 (1H, t9, Glc-3α), δ6.22 (1H, s, HHDP), δ6.27 (1H, s, HHDP), 66.77 (2H, s, gallate-2, 6), δ6.79 (1H, s, D-3"), δ6.83 (1H, d2, A-6), δ6.85 (2H, s, gallate-2, 6), δ7.03 (1H, d2, A-8) and δ7.87 (2H, s, B-2', 6'). HHDP is the abbreviation for hexahydroxy diphenoyl. In addition, a hydroxyl group at position 1 of the sugar was observed as a minor signal among the signals of β type glucose.

Figure 13:
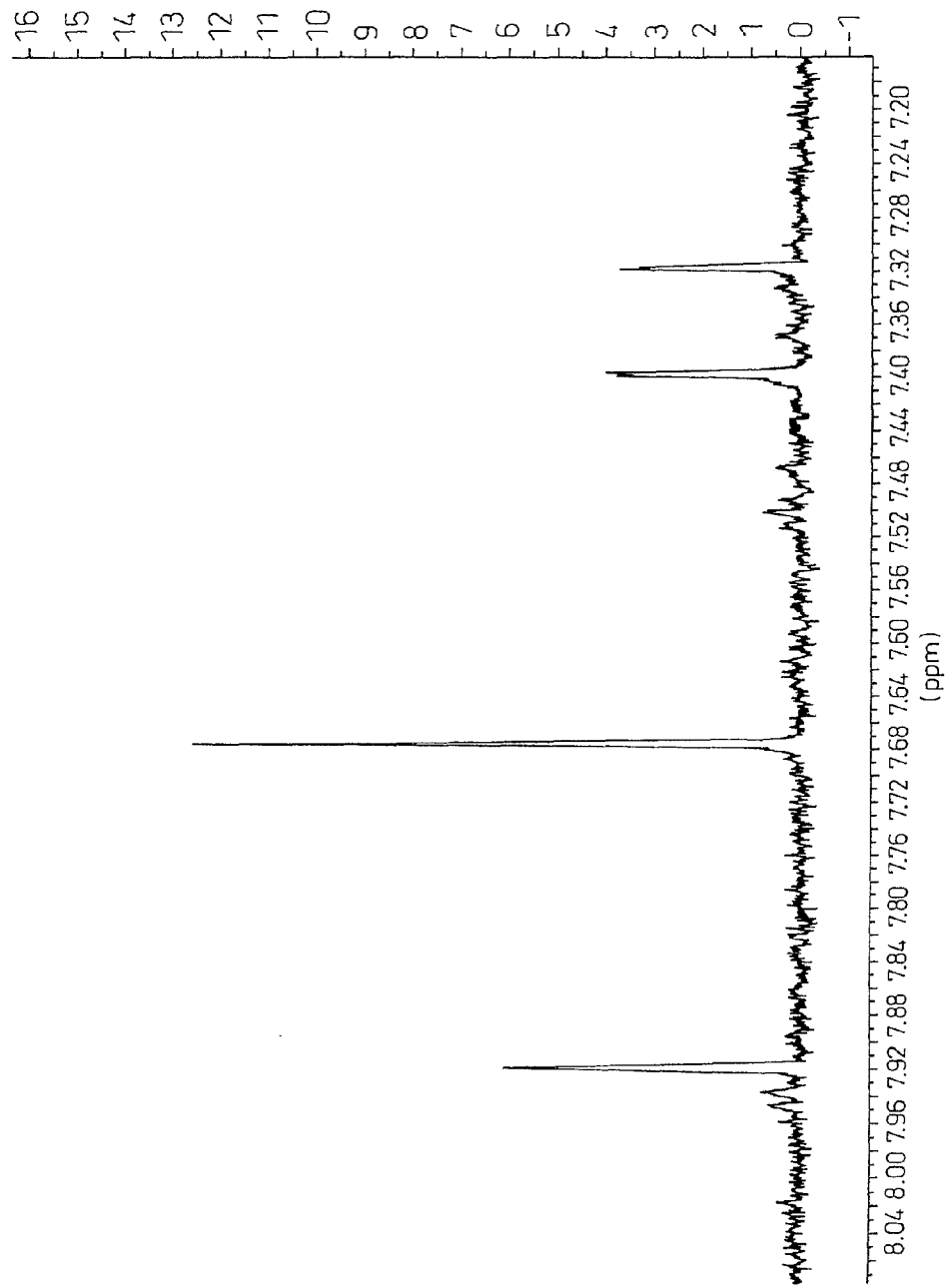
FIG. 13 is a chart of the $^1$H-NMR spectrum of the red pigment (2) shown in FIG. 9.
Figure 14:
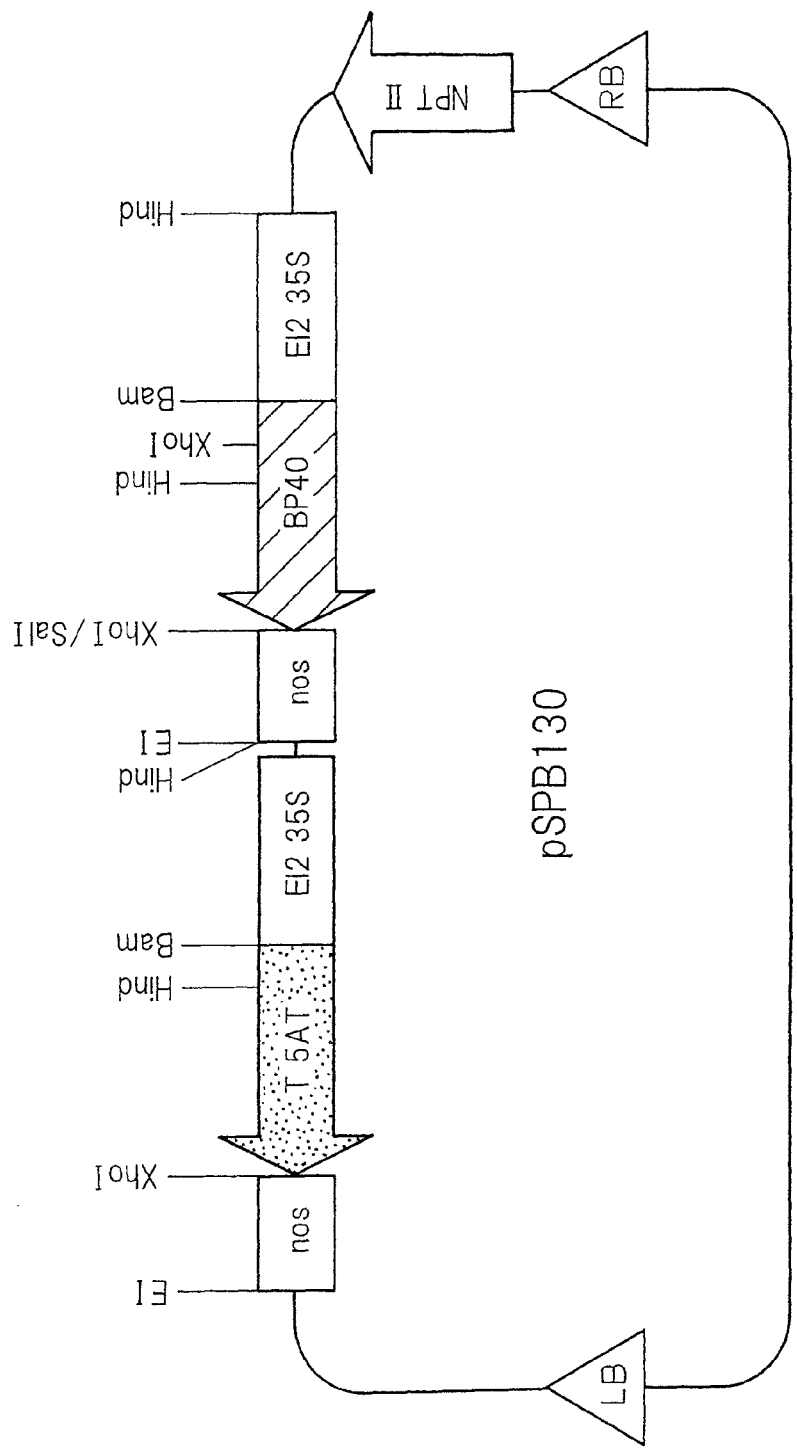
FIG. 14 indicates the structure of plasmid pSPB130 transfected into mauve rose variety "WKS82".

The results of $^1$H-NMR analysis of the red pigment (2) are shown in FIG. 13.

In the case of the red pigment (2), signals during $^1$H-NMR were observed at δ7.32 (1H, d1.5, A-6), δ7.40 (1H, d1.5, A-8), δ7.68 (2H, s, B-2', 6') and δ7.92 (1H, s, D-3").

Example 3

Confirmation of Pigment Compounds in Different Variety of Blue Rose

The presence of compounds of the present invention was confirmed for a variety of blue rose different from that of Example 1.

Production of Variety "WKS82" Transfected with Plasmid pSPB130

Variety "WKS82" transfected with plasmid pSPB130 was produced according to the method described below.

Anthocyanins can be stabilized and made to demonstrate a blue color by modifying with an aromatic acyl group (see, for example, WO 96/25500). The following experiment was conducted for the purpose of producing an acylated delphinidin-type anthocyanin.

RNA was obtained from the flower petals of the torenia variety "Summer wave", and poly-A RNA was further prepared from this RNA. A cDNA library using λZAPII (Stratagene) as a vector was prepared from this poly-A RNA using a directional cDNA library production kit (Stratagene) in accordance with the method recommended by the manufacturer. Since the main anthocyanin of torenia has glucose at position 5 thereof modified by an aromatic acyl group (Suzuki, et al., Molecular Breeding, 6, 239-246, 2000), anthocyanin acyltransferase is expressed in torenia flower petals.

Anthocyanin acyltransferase retains a specific amino acid sequence, and anthocyanin acyltransferase gene can be acquired by using synthetic DNA corresponding thereto as primer (WO 96/25500). More specifically, PCR was carried out under the conditions recommended by the manufacturer using 10 ng of single-stranded cDNA synthesized during production of the torenia cDNA library as template, using 100 ng of ATC primer (see SEQ ID NO. 17 of Patent Document 2) and 100 ng of oligo dT primer (see SEQ ID NO. 18 of Patent Document 2) as primers, and using Taq polymerase (Takara, Japan).

PCR was carried out for 25 cycles consisting of 1 minute at 95° C., 1 minute at 55° C. and 1 minute at 72° C. The resulting roughly 400 bp DNA fragment was recovered with GeneClean II (Bio 101 Inc.) according to the method recommended by the manufacturer, and sub-cloned into pCR-TOPO. When the nucleotide sequence thereof was determined, a sequence was found that was homologous with the acyltransferase gene of Japanese gentian (Fujiwara, et al., Plant J., 16, 421-431, 1998). Furthermore, the nucleotide sequence was determined according to the dye-primer method (Applied Biosystems) using a Sequencer 310 or 377 (Applied Biosystems).

This DNA fragment was labeled with a DIG label detection kit (Nippon Roche), and a torenia cDNA library was screened using the plaque hybridization method according to the method recommended by the manufacturer. Twelve of the resulting clones that demonstrated positive signals were randomly selected, and plasmids were recovered from the clones followed by determination of the nucleotide sequences. These sequences demonstrated favorable homology with anthocyanin acyltransferase. Among these clones, the entire nucleotide sequence was determined for cDNA contained in the clone designated as pTAT7 (refer to SEQ ID NO. 7 of Patent Document 2 for the nucleotide sequence, and SEQ ID NO. 8 of Patent Document 2 for the amino acid sequence).

pBE2113-GUS (Mitsuhara, et al., Plant Vell. Physiol., 37, 45-59, 1996) was digested with SacI followed by blunting and inserting an 8 bp XhoI linker. A roughly 1.7 kb DNA fragment obtained by digesting pTAT7 with BamHI and XhoI was inserted at the BamHI and XhoI sites of this plasmid to obtain pSPB120. pSPB120' was obtained by digesting pSBP120 with SanBI and BamHI followed by blunting and ligation. On the other hand, plasmid pCGP1961 containing pansy-derived F3'5'H#40 cDNA was completely digested with BamHI and then partially digested with XhoI, the resulting roughly 1.8 kb DNA fragment was recovered, this was then ligated with pUE5H digested with BamHI and XhoI, and the resulting plasmid was designated as pUEBP40.

pUEBP40' was obtained by digesting pEUBP40 with SnaBI and BamHI followed by blunting and ligation. The pUEBP40' was partially digested with HindIII, and the resulting roughly 2.7 kb DNA fragment was recovered and then ligated with a DNA fragment obtained by partially digesting pSPB120' with HindIII. Among the resulting plasmids, a binary vector in which neomycin phosphotransferase gene, pansy-derived F3'5'H#40 gene and torenia-derived 5AT gene were ligated in that order from the right border of the binary vector was designated as pSPB130 (see FIG. 12). This plasmid is designed to constitutively express pansy-derived F3'5'H#40 gene and torenia-derived 5AT gene in plants, and specifically transcribe the genes in flower petals. This plasmid was transfected into Agrobacterium tumefaciens strain Ag10. As a result of infecting this Agrobacterium strain, pSPB130 (FIG. 12) was transfected into mauve rose variety "WKS82" to obtain a transformant. The transformed cells were then regenerated to obtain a recombinant plant in the form of a blue rose (variety "WKS82" transfected with plasmid pSPB130) and this was then allowed to bloom.

Extraction, Isolation, Purification and Identification of Pigment Compounds

Extraction, isolation and purification were carried out on 230 g of flower petals of the blue rose obtained in the manner described above (variety "WKS82" transfected with plasmid pSPB130) using the same method as that of Example 1 to obtain blue pigment (1), the red pigment (2) and the blue pigment (3).

The blue pigment (1), the red pigment (2) and the blue pigment (3) were visually observed for color tone. As a result, they demonstrated a deep blue, deep red, and deep blue color, respectively.

In addition, the blue pigment (1), the red pigment (2) and the blue pigment (3) were confirmed to respectively be the same compounds as the pigment components identified in Example 1 by using LC-TOF-MS.

INDUSTRIAL APPLICABILITY

According to the present invention, a novel pigment present in the flower petals of the blue roses was extracted, isolated and purified, and its chemical structure was elucidated. The compound newly discovered in the present invention demonstrates a bluer color than rosacyanins known to be present in conventional mauve-colored roses. Accordingly, the flower color of a plant can be altered by using this compound discovered in the present invention. Alternatively, this compound can also be used to can be used to color foods and beverages, for example, by using as a plant pigment.

4. A purified compound represented by the following formula:
[Chemical Formula 6]
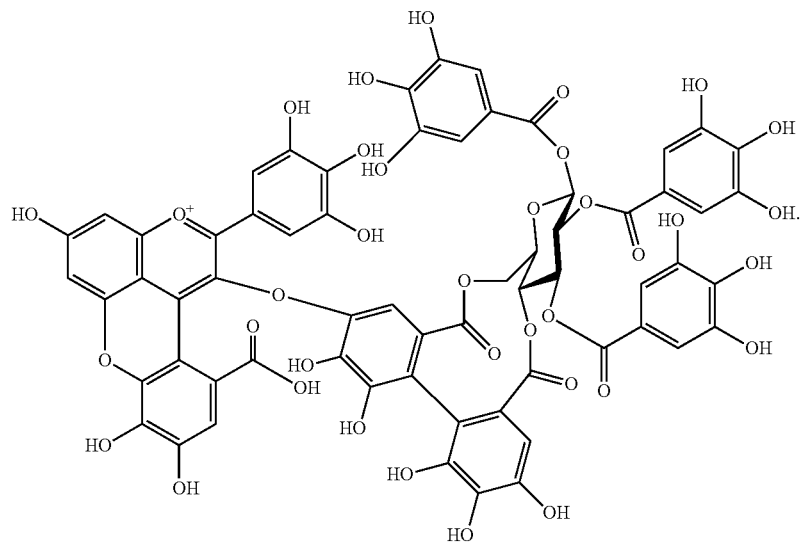

The invention claimed is:

1. A purified compound represented by the following general formula (I):

[Chemical Formula 1]

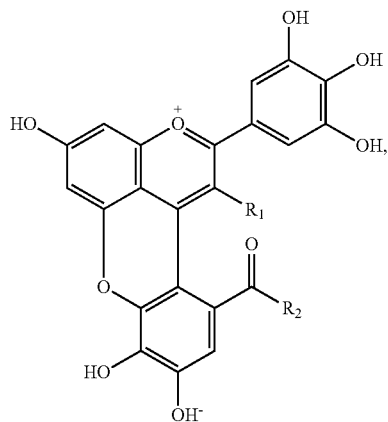

wherein, $R_1$ represents the following group:

[Chemical Formula 2]

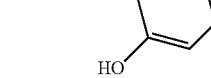

and $R_2$ represents —OH or $R_1$ and $R_2$ together form —O—, or $R_1$ represents the following group:

[Chemical Formula 3]

and $R_2$ represents —OH, provided that the coordination (wavy line) of the hydroxyl group at position 1 of glucose in $R_1$ exhibits tautomerism between the α form and the β form.

2. A purified compound represented by the following formula:

[Chemical Formula 4]

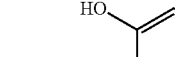

3. A purified compound represented by the following formula:

[Chemical Formula 5]